(12) United States Patent
Kim (10) Patent No.: US 12,257,170 B2
(45) Date of Patent: Mar. 25, 2025

(54) FUNCTIONAL JOINT ASSIST APPARATUS

(71) Applicant: KOREA UNIVERSITY RESEARCH AND BUSINESS FOUNDATION, Seoul (KR)

(72) Inventor: Jae Gyoon Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 897 days.

(21) Appl. No.: 17/291,710

(22) PCT Filed: Oct. 2, 2019

(86) PCT No.: PCT/KR2019/012901
§ 371 (c)(1),
(2) Date: May 6, 2021

(87) PCT Pub. No.: WO2020/096204
PCT Pub. Date: May 14, 2020

(65) Prior Publication Data
US 2022/0000650 A1  Jan. 6, 2022

(30) Foreign Application Priority Data
Nov. 7, 2018 (KR) .......... 10-2018-0135953

(51) Int. Cl.
*A61F 5/058* (2006.01)
*A61F 7/00* (2006.01)
*A61F 7/02* (2006.01)

(52) U.S. Cl.
CPC .......... *A61F 5/05816* (2013.01); *A61F 7/02* (2013.01); *A61F 2007/0062* (2013.01); *A61F 2007/0231* (2013.01)

(58) Field of Classification Search
CPC ............ A61F 5/05816; A61F 7/02; A61F 2007/0062; A61F 2007/0231; A61F 2007/0042; A61F 2007/0055; A61F 5/01; A61F 5/058; A61F 5/34; A61F 5/0123; A61F 5/0585; A61F 2007/0091; A61F 5/012; A61B 17/135; A47C 27/10
See application file for complete search history.

(56) References Cited

U.S. PATENT DOCUMENTS 3,901,225 A * 8/1975 Sconce ............... A61F 5/05816
128/DIG. 20
5,314,455 A   5/1994 Johnson, Jr. et al.
(Continued)

FOREIGN PATENT DOCUMENTS

KR   10-2010-0005505   1/2010
WO   WO 02-19954      3/2002

OTHER PUBLICATIONS

International Search Report mailed Jan. 29, 2020 for PCT/KR2019/012901.
(Continued)

*Primary Examiner* — Ophelia A Hawthorne (57) ABSTRACT

The present disclosure relates to a functional joint assist apparatus including an air bladder having a cut hole and divided into a plurality of air cells so that air is injected into at least one of the air cells; and a fixing unit coupled to a front surface or a rear surface of the air bladder to attach or detach the air bladder to/from the joint.

12 Claims, 5 Drawing Sheets

(56) References Cited

U.S. PATENT DOCUMENTS

| | | | |
|---|---|---|---|
| 5,466,250 A | 11/1995 | Johnson, Jr. et al. | |
| 5,489,259 A * | 2/1996 | Jacobs | A61F 5/012 |
| | | | 128/DIG. 20 |
| 5,752,927 A * | 5/1998 | Rogachevsky | A61F 5/012 |
| | | | 602/18 |
| 7,468,048 B2 | 12/2008 | Meehan | |
| 2007/0161932 A1 | 7/2007 | Pick et al. | |
| 2013/0331753 A1* | 12/2013 | Farrow | A61F 5/012 |
| | | | 602/16 |
| 2018/0000626 A1* | 1/2018 | Deren | A61F 5/05816 |

OTHER PUBLICATIONS

Office Action dated Apr. 27, 2020 corresponding to Korean Application No. 10-2018-0135953, 3 pages.

* cited by examiner

FIG. 1

< Prior Art >

FUNCTIONAL JOINT ASSIST APPARATUS

This application claims the priority of Korean Patent Application No. 10-2018-0135953, filed on Nov. 7, 2018 in the KIPO (Korean Intellectual Property Office), the disclosure of which is incorporated herein entirely by reference. Further, this application is the National Stage application of International Application No. PCT/KR2019/012901, filed on Oct. 2, 2019, which designates the United States and was published in Korean. Each of these applications is hereby incorporated by reference in their entirety into the present application.

TECHNICAL FIELD

This disclosure relates to a functional joint assist apparatus, and more specifically, to a functional joint assist apparatus that may be selectively applied according to joint rehabilitation and may perform physical treatment through hot and cold steaming

BACKGROUND ART

Biological joints, such as the human knee joint, are vital to the well-being of the individual. In the human knee joint, the anterior cruciate ligament (ACL) and posterior cruciate ligament (PCL) are particularly vulnerable to injury. After injury or surgical procedure, an assister is often used for the purpose of protecting the anterior cruciate ligament or posterior cruciate ligament while still allowing joint movement. These assisters can be classified as an anterior cruciate ligament assister or a posterior cruciate ligament assister depending on their intended purpose.

Figure 1:
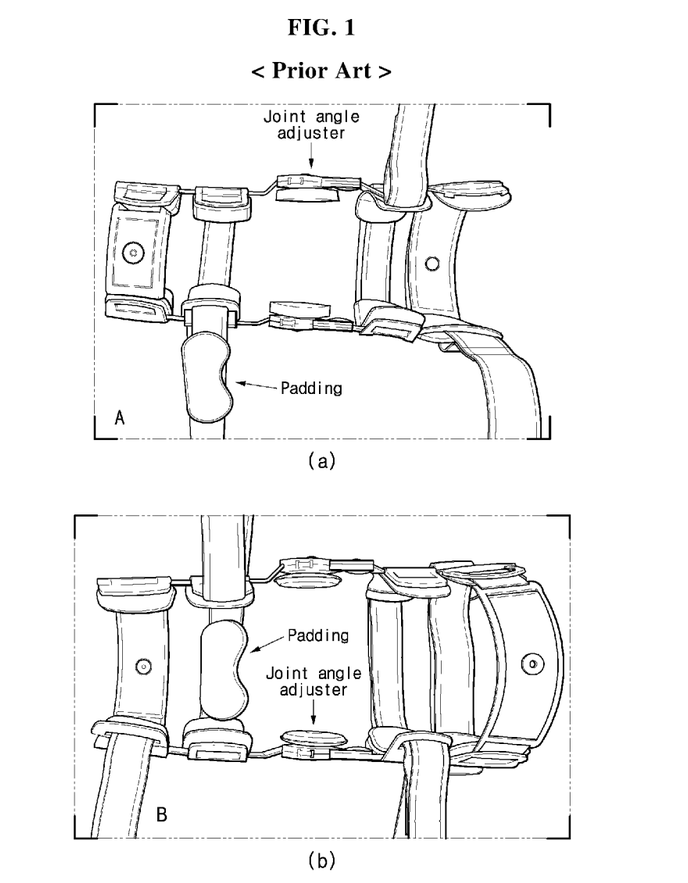
FIG. 1 illustrates existing joint as sisters.

In the anterior cruciate ligament assister ((a) of FIG. 1), an aluminum beam at the thigh side is located in the rear, and an aluminum beam at the calf side is located in the front. A padding is located in the front to prevent the anterior displacement of the tibia. In the posterior cruciate ligament assister ((b) of FIG. 1), the aluminum beam at the thigh side is located in the front, and the aluminum beam at the calf side is located in the rear. A padding is located in the front to prevent the posterior translation of the tibia.

However, since the padding attached to the as sister has a fixed thickness regardless of the thickness or length of the leg of a patient, the effect of the padding decreases depending on the flexion or extension of the knee joint, resultantly deteriorating the effect of the assister. Also, since the assister is fixed to the leg of the patient by means of a frame and hook and loop fasteners, the as sister is not firmly adhered to the leg of the patient and therefore slips down during use. Because of this slippage, it is difficult to effectively prevent the anteroposterior dislocation of the patient.

In addition, it is difficult to change the anterior cruciate ligament as sister to the posterior cruciate ligament assister, and it is difficult for the patient to change it directly, so replacement work must be done by a specialist. For this reason, some patients use both as sisters.

Meanwhile, since the knee assister is designed only for knee injury or rehabilitation after surgery, a separate device must be employed to apply heat or cold to reduce swelling and pain around the knee. This is not only cumbersome but also inconvenient for the patient.

It would therefore be advantageous to have a device which avoided some or all of the problems of existing devices.

DISCLOSURE OF THE INVENTION

Technical Problem

This disclosure is directed to providing a functional joint assist apparatus that may be selectively applied according to a joint more conveniently and may perform physical treatment through hot and cold steaming.

The object of the present disclosure is not limited to the above, other objects not mentioned herein will be clearly understood from the following disclosure by those skilled in the art.

Technical Solution

In order to achieve the above object, a functional joint assist apparatus according to an embodiment of the present disclosure, which is disposed inside a joint assister to assist the joint assister, includes an air bladder having a cut hole and divided into a plurality of air cells so that air is injected into at least one of the air cells; and a fixing unit coupled to a front surface or a rear surface of the air bladder to attach or detach the air bladder to/from the joint.

Here, the air bladder may include a first air cell formed at an upper side with respect to the cut hole and having a first air injection hole; a second air cell having a second air injection hole and formed narrower than a width of a lower side of the first air cell; and a third air cell having a third air injection hole and extending outward from both side surfaces of the second air cell and located at the rear of the calf when surrounding the joint of a user, wherein the second air cell may compress a front side of the shin of the user when air is injected therein and both side surfaces of the third air cell may compress a rear side of the calf of the user when air is injected therein.

Here, the joint of the user may be any one of a knee, an elbow, a wrist, an ankle, a neck, a shoulder and a waist in which two or more bones are connected in contact with each other.

Here, the first air cell, the second air cell and the third air cell may be integrally formed and be partitioned so that air does not communicate with each other.

Here, a steam pack providing cold steaming or hot steaming may be further provided at the other side of the air bladder to which the fixing unit is attached.

Here, the fixing unit may be made of a strip-shaped hook and loop fastener material and coupled to upper and lower sides of the air bladder based on the cut hole.

Advantageous Effects

In the functional joint assist apparatus according to the present disclosure, an air bladder including a first air cell, a second air cell and a third air cell is disposed inside the joint assister, so that air is selectively injected into each air cell according to the purpose of rehabilitation for joint reconstruction of the user, so it is possible to provide two types of rehabilitation treatments by using one joint as sister.

In addition, since the frame and the hook and loop fastener of the as sister are firmly adhered in close contact with the leg of the patient by means of the plurality of inflated air cells, it is possible to support the frame and the hook and loop at proper positions for joint reconstruction, preventing the assister from slipping.

Moreover, in the present disclosure, since heat treatment or cold treatment may be performed together in a state where the user is wearing the joint assister, the damaged area of the user may be recovered more quickly.

The effects of the present disclosure are not limited to the above-mentioned effects, and other effects not mentioned herein will be clearly understood by those skilled in the art from the following description.

BEST MODE FOR CARRYING OUT THE INVENTION

Hereinafter, a preferred embodiment of the present disclosure will be described in detail with reference to the accompanying drawings. In this case, it should be noted that in the accompanying drawings, like components are indicated by like reference numerals as possible. In addition, a detailed description of the known function and configuration that may obscure the gist of the present disclosure will be omitted. For the same reason, some elements in the accompanying drawings are exaggerated, omitted or schematically illustrated.

In addition, throughout the specification, when a part is explained as "including" a certain component, it means that other components may be further included rather than excluding other components, unless specifically stated to the contrary. In addition, throughout the specification, the term "on" means that a component is positioned above or below a target portion, and does not necessarily mean that it is positioned above based on the direction of gravity.

In the present disclosure, the term "joint" is a region where two or more bones are in contact with each other, and it is not specially limited as long as movements such as circumduction, rotation, gliding motion and adduction are possible in the region. Hereinafter, a functional joint assist apparatus according to an embodiment of the present disclosure is described as an example as being mounted on the knee as sister to rehabilitate the anterior cruciate ligament or posterior cruciate ligament of the knee, but it may also be applied to an elbow, a wrist, an ankle, a neck, a shoulder, a waist, and the like, where a joint may be treated by selectively changing a compressing location on the body through air injection and simultaneously a physical treatment may be performed through hot and cold steaming.

Figure 2:
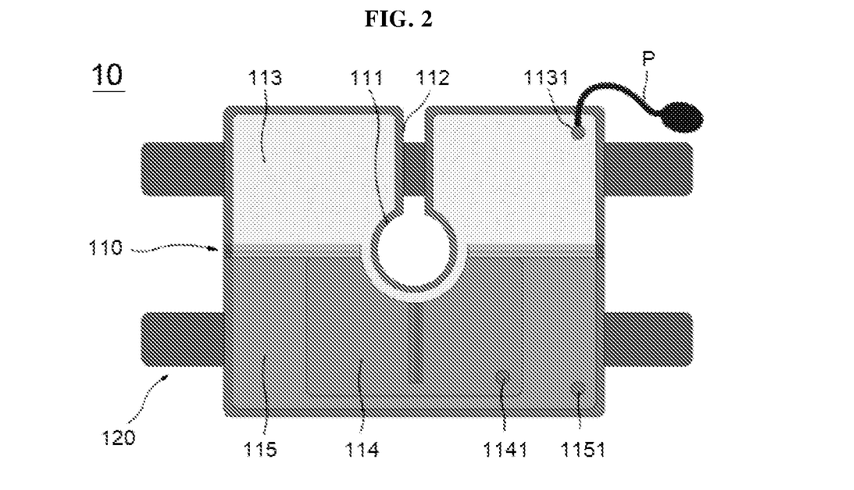
FIG. 2 is a diagram showing a functional joint assist apparatus according to an embodiment of the present disclosure.

FIG. 2 is a diagram showing a functional joint assist apparatus according to an embodiment of the present disclosure.

Referring to FIG. 2, the functional joint assist apparatus 10 according to an embodiment of the present disclosure is disposed inside a knee assister 1 (FIG. 5) to assist the knee as sister, and includes an air bladder 110 and a fixing unit 120.

The air bladder 110 has a cut hole 111 formed at a position corresponding to the patella, and is divided into a plurality of air cells 113, 114, 115 so that air is injected into at least one of the air cells 113, 114, 115. The cut hole 111 is formed in an approximately circular shape, and a band-shaped open cut portion 112 is formed in an upper surface of the cut hole 111 toward an upper side so as to be in close contact with the knee. The fixing unit 120 is attached to the air bladder 110 in contact with the knee to make the air bladder 110 surround the knee. The fixing unit 120 is made of a strip-shaped hook and loop fastener material and may be coupled to an upper side and a lower side of the front surface or the rear surface of the air bladder 110 based on the cut hole 111.

Hereinafter, the air bladder 110 will be described in more detail with reference to the drawings.

Figure 3:
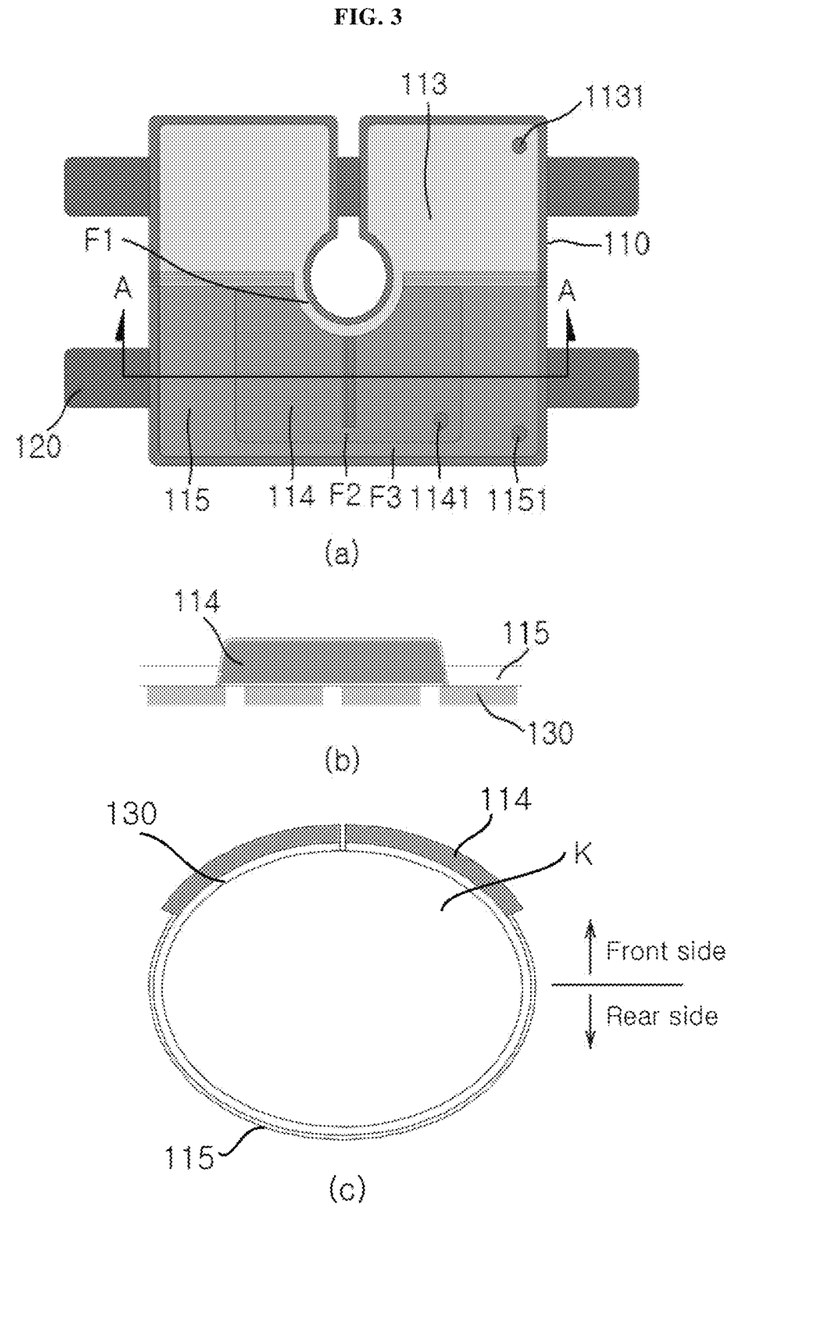
FIG. 3 is a sectional view showing a state where a second air cell of the functional joint assist apparatus according to an embodiment of the present disclosure is inflated and worn.
Figure 4:
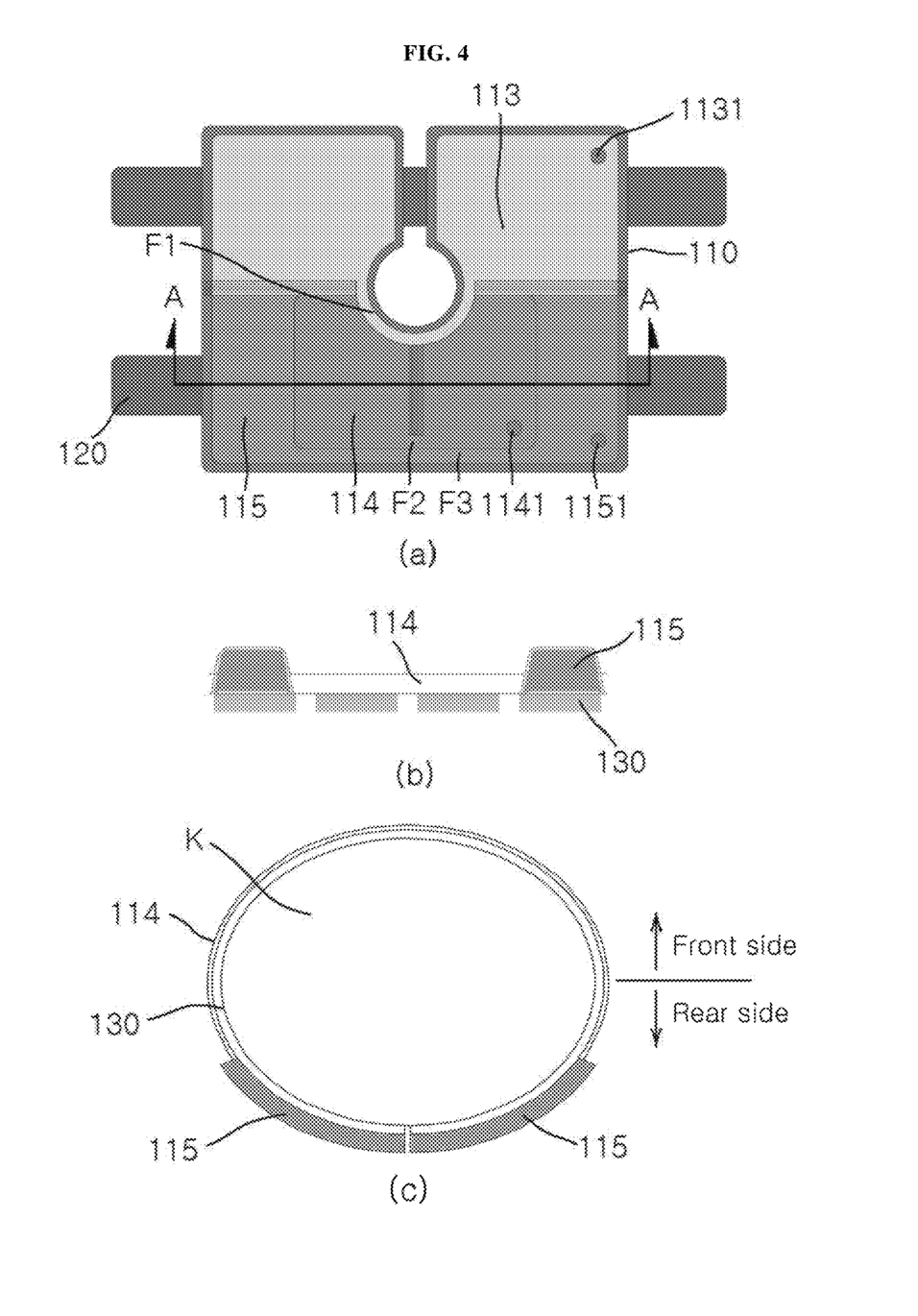
FIG. 4 is a sectional view showing a state where a third air cell of the functional joint assist apparatus according to an embodiment of the present disclosure is inflated and worn.
Figure 5:
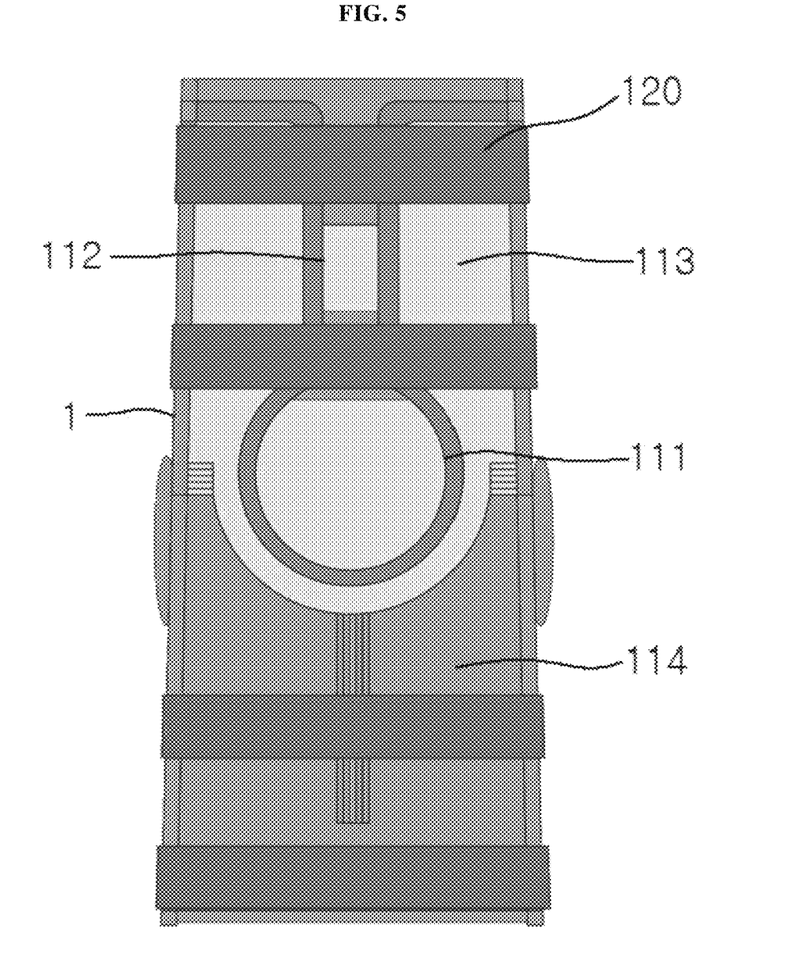
FIG. 5 is a diagram showing a state where the functional joint assist apparatus according to an embodiment of the present disclosure is worn.
Figure 6:
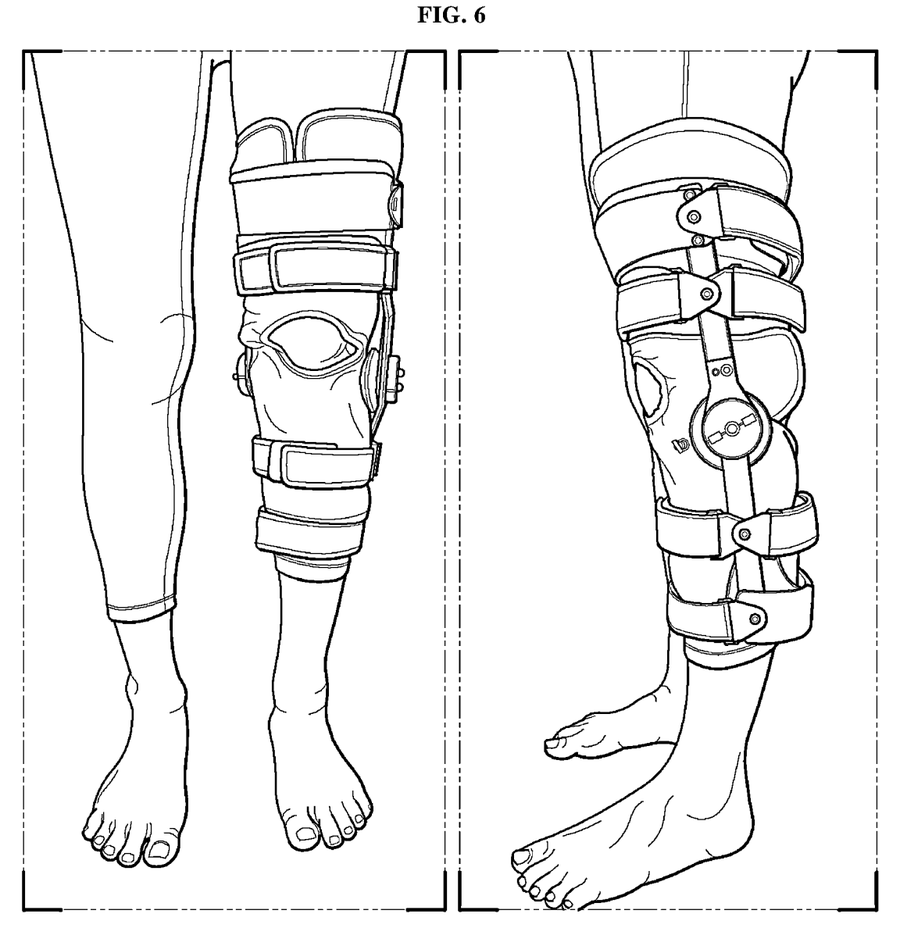
FIG. 6 is a photograph showing a state where the functional joint assist apparatus according to an embodiment of the present disclosure is worn.

FIG. 3 is a sectional view showing a state where a second air cell of the functional joint assist apparatus according to an embodiment of the present disclosure is inflated and worn; FIG. 4 is a sectional view showing a state where a third air cell of the functional joint assist apparatus according to an embodiment of the present disclosure is inflated and worn; FIG. 5 is a diagram showing a state where the functional joint assist apparatus according to an embodiment of the present disclosure is worn; and FIG. 6 is a photograph showing a state where the functional joint assist apparatus according to an embodiment of the present disclosure is worn.

Referring to FIGS. 2 to 6, the air bladder 110 according to an embodiment of the present disclosure includes a first air cell 113, a second air cell 114, and a third air cell 115.

The first air cell 113 is formed at an upper side based on the cut hole 111 and has a first air injection hole 1131. Air is injected through the first air injection hole 1131 by means of a pump P. The first air injection hole 1131 is formed only at one side of the first air cell 113 formed symmetrically, and the air is moved along a flow path F1 formed in a lower circumferential direction of the cut hole 111 to be uniformly supplied into the entire inside of the first air cell 113. The first air cell 113 is integrally formed with the second air cell 114 and the third air cell 115, but is partitioned therefrom so that air does not communicate with each other.

The first air cell 113 into which air is completely injected surrounds an upper area of the knee K (with respect to the kneecap) including the distal thigh. The second air cell 114 and the third air cell 115, explained later, may be selectively filled with air, but the first air cell 113 is always filled with air to firmly fix the knee assister 1 to the patient's leg so as not to slip down, along with the second air cell 114 and third air cell 115 selectively filled with air.

The second air cell 114 has a second air injection hole 1141 and is formed narrower than a width of a lower side of the first air cell 113. That is, the second air cell 114 extends symmetrically at the lower side of the first air cell 113 toward both sides to roughly surround a front area of the knee from the center of the cut hole 111. Air is injected through the second air injection hole 1141 by means of the pump P. The second air injection hole 1141 is formed only at one side of the second air cell 114, and the air is moved along a flow path F2 formed at a lower side of the second air cell 114 to be uniformly supplied to the entire inside of the second air cell 114.

The second air cell 114 into which air is completely injected surrounds a front region of the lower of the knee (with respect to the kneecap) as shown in FIG. 3(c) so as to compress the front side of the proximal tibia of the user to prevent anterior translation of the tibia. As described above, the second air cell 114 may protect the anterior cruciate ligament reconstructed after the surgery of the anterior cruciate ligament by compressing the front side of the proximal tibia of the user. When the second air cell 114 is filled with air to protect the anterior cruciate ligament, it is desirable that the third air cell 115 is emptied contrary to the second air cell 114.

The third air cell 115 has a third air injection hole 1151 and extends outward from both side surfaces of the second air cell 114. The third air cell 115 extends bi-directionally symmetrically enough to surround a rear area at both side surfaces of the second air cell 114. Air is injected through the third air injection hole 1151 by means of the pump P. The third air injection hole 1151 is formed only at one side of the third air cell 115 formed symmetrically, and the air is moved along a flow path F3 formed at a lower side of the third air cell 115 to be uniformly supplied to the entire inside of the third air cell 115. In this way, the injected third air cell 115 into which air is injected is disposed so that both side surfaces of the third air cell 115 surround the rear side of the knee in a state where air is injected therein.

The third air cell 115 into which air is completely injected surrounds the rear area of proximal calf, as shown in FIG. 4(c) to compress the rear side of the knee of the user to prevent posterior displacement the tibia of the user. As such, the third air cell 115 may compress the rear side of the proximal calf of the user, thereby protecting the posterior cruciate ligament through reconstruction of the posterior cruciate ligament. For protecting the posterior cruciate ligament, when the third air cell 115 is filled with air, it is desirable that the second air cell 114 is emptied contrary to the third air cell 115.

As described above, the air bladder 110 (including the first air cell 113, the second air cell 114 and the third air cell 115) is disposed inside the knee assister 1 according to the rehabilitation purpose for the reconstruction of the anterior cruciate ligament or posterior cruciate ligament of the user so that air is selectively injected into each air cell, so one knee assister 1 may provide two types of rehabilitation treatment. In addition, since the frame and the hook and loop fastener of the assister are firmly fixed in close contact with the leg of the patient by means of the plurality of inflated air cells, it is possible to support the frame and the hook and loop fastener at proper positions for reconstruction of the anterior cruciate ligament or posterior cruciate ligament and prevent the assister from slipping down the patient's leg (see FIG. 6).

The present disclosure may further include a steam pack 130 for providing cold steaming or hot steaming at the other side of the air bladder 110 to which the fixing unit 120 is attached. The steam pack 130 may be detachably attached to the air bladder 110 through a hook and loop fastener structure. The steam pack 130 has a hole corresponding to the cut hole 111 of the air bladder 110. Therefore, in the present disclosure, heat treatment or cold treatment may be performed simultaneously in a state where the user is wearing the knee assister, so the damaged ligament area of the user may be recovered more quickly.

The embodiments of the present disclosure disclosed in this specification and drawings are merely specific examples to easily explain the technical content of the present disclosure and to help the understanding of the present disclosure, and is not intended to limit the scope of the present disclosure. It is obvious to those skilled in the art that other modifications can be made based on the technical idea of the present disclosure in addition to the embodiments disclosed herein.

The invention claimed is:

1. A functional joint assist apparatus disposed inside a joint assister for assisting the joint assister, comprising:
   an air bladder comprising:
      a front surface;
      a rear surface;
      a cut hole passing through a thickness of the air bladder from the front surface to the rear surface, and
      a plurality of air cells partitioned so that air does not communicate between the air cells, wherein air is injected into at least one of the plurality of air cells, the plurality of air cells comprising:
         a first air cell formed at an upper side based on the cut hole and configured to surround and compress an upper side of a user's joint;
         a second air cell formed at a lower side based on the cut hole and configured to surround and compress at least a portion of a lower side of the user's joint; and
         a third air cell formed at a lower side based on the cut hole and configured to surround and compress at least a portion of the lower side of the patient's joint different from the portion that the second air cell is configured to surround and compress,
      wherein at least one air cell is divided into a left portion and a right portion,
      wherein a flow path connects the left portion and the right portion; and
   a fixing unit coupled to either the front surface or the rear surface of the air bladder for attaching the air bladder to the joint.

2. The functional joint assist apparatus of claim 1, wherein a width of the second air cell is narrower than a width of a lower side of the first air cell, and the third air cell extends outward from the width of the second air cell.

3. The functional joint assist apparatus of claim 1, wherein the fixing unit comprises a plurality of hook and loop fasteners.

4. The functional joint assist apparatus of claim 1, wherein the plurality of air cells are integrally formed in the air bladder.

5. The functional joint assist apparatus of claim 1, wherein the first air cell comprises a first air injection hole, the second air cell comprises a second air injection hole, and the third air cell comprises a third air injection hole.

6. The functional joint assist apparatus of claim 1, wherein the joint of the user is any one of a knee, an elbow, a wrist, an ankle, a neck, a shoulder and a waist in which two or more bones are connected in contact with each other.

7. The functional joint assist apparatus of claim 1, further comprising:
   a steam pack for providing cold steaming or hot steaming.

8. A functional joint assist apparatus disposed inside a joint assister for assisting the joint assister, comprising:
   an air bladder having a cut hole and divided into a plurality of air cells partitioned so that air does not communicate between the air cells and so that air is injected into at least one of the air cells, the air bladder comprising:
      a first air cell formed at an upper side based on the cut hole and having a first air injection hole;

a second air cell formed at a lower side based on the cut hole and having a second air injection hole and formed narrower than a width of a lower side of the first air cell; and a third air cell formed at a lower side based on the cut hole and having a third air injection hole and extending outward from both side surfaces of the second air cell and located at the rear of the joint when surrounding the joint of a user, wherein the second air cell compresses a front side of the joint of the user when air is injected therein, wherein both side surfaces of the third air cell compresses a rear side of the joint of the user when air is injected therein, wherein at least one air cell is divided into a left portion and a right portion, wherein a flow path connects the left portion and the right portion; and a fixing unit coupled to a front surface or a rear surface of the air bladder for attaching the air bladder to the joint.

9. The functional joint assist apparatus of claim 8, wherein the joint of the user is any one of a knee, an elbow, a wrist, an ankle, a neck, a shoulder and a waist in which two or more bones are connected in contact with each other.

10. The functional joint assist apparatus of claim 8, wherein the first air cell, the second air cell and the third air cell are integrally formed.

11. The functional joint assist apparatus of claim 8, wherein a steam pack providing cold steaming or hot steaming is further provided at an opposite side of the air bladder to which the fixing unit is attached.

12. The functional joint assist apparatus of claim 8, wherein the fixing unit is made of a strip-shaped hook and loop fastener material and coupled to upper and lower sides of the air bladder based on the cut hole.

\* \* \* \* \*